United States Patent
Chien

(10) Patent No.: US 10,162,082 B2
(45) Date of Patent: Dec. 25, 2018

(54) OPHTHALMIC LENS MATERIAL AND OPHTHALMIC LENS OF SUCH MATERIAL

(71) Applicant: MiiCs & Partners (Shenzhen) Co., Ltd., Shen Zhen (CN)

(72) Inventor: Hsiu-Wen Chien, New Taipei (TW)

(73) Assignee: MiiCs & Partners (Shenzhen) Co., Ltd., Shenzhen (CN)

( * ) Notice: Subject to any disclaimer, the term of this patent is extended or adjusted under 35 U.S.C. 154(b) by 0 days.

(21) Appl. No.: 15/497,211

(22) Filed: Apr. 26, 2017

(65) Prior Publication Data

US 2018/0210114 A1 Jul. 26, 2018

(30) Foreign Application Priority Data

Jan. 20, 2017 (TW) .............................. 106102051 A

(51) Int. Cl.

| | | |
|---|---|---|
| G02B 1/04 | (2006.01) | |
| C08G 77/04 | (2006.01) | |
| C08K 3/24 | (2006.01) | |
| C07F 9/53 | (2006.01) | |
| C07F 7/08 | (2006.01) | |
| C07D 303/16 | (2006.01) | |
| C07D 207/267 | (2006.01) | |
| C07C 245/22 | (2006.01) | |
| C07C 233/09 | (2006.01) | |
| C07C 69/604 | (2006.01) | |
| C07C 69/602 | (2006.01) | |
| C07C 69/54 | (2006.01) | |
| C07C 49/84 | (2006.01) | |
| C07C 49/83 | (2006.01) | |

(Continued)

(52) U.S. Cl.
CPC .............. *G02B 1/043* (2013.01); *C07C 43/16* (2013.01); *C07C 49/82* (2013.01); *C07C 49/83* (2013.01); *C07C 49/84* (2013.01); *C07C 69/54* (2013.01); *C07C 69/602* (2013.01); *C07C 69/604* (2013.01); *C07C 233/09* (2013.01); *C07C 245/22* (2013.01); *C07D 207/267* (2013.01); *C07D 303/16* (2013.01); *C07F 7/0838* (2013.01); *C07F 7/0852* (2013.01); *C07F 9/5333* (2013.01); *C08G 77/04* (2013.01)

(58) Field of Classification Search
USPC ................................... 523/107, 106; 528/25
See application file for complete search history.

(56) References Cited

U.S. PATENT DOCUMENTS

| | | | | |
|---|---|---|---|---|
| 4,971,732 A | * | 11/1990 | Wichterle | ............. A61F 2/1613 264/1.1 |
| 2011/0009519 A1 | * | 1/2011 | Awasthi | ................ C08F 226/08 523/107 |

(Continued)

FOREIGN PATENT DOCUMENTS

WO WO 01/05578 * 1/2001

*Primary Examiner* — Tae H Yoon
(74) *Attorney, Agent, or Firm* — ScienBiziP, P.C.

(57) ABSTRACT

A wetness-retaining ophthalmic lens material comprises an organic monomer, a cross-linking agent, an initiator, a salt, and a solvent. The salt dissolves in the water dissociates a plurality of anions and cations, which bind to water molecules and retard the evaporation of the water molecules, the ophthalmic lens material thus can keep wet for a long time. An ophthalmic lens made of the ophthalmic lens material is also provided.

8 Claims, 1 Drawing Sheet

(51) Int. Cl.
    *C07C 49/82* (2006.01)
    *C07C 43/16* (2006.01)

(56) References Cited

U.S. PATENT DOCUMENTS

2012/0272866 A1* 11/2012 Wang .................. C08J 9/26
                                                    106/122
2014/0221523 A1* 8/2014 Jan .................. C08F 230/08
                                                    523/107

* cited by examiner

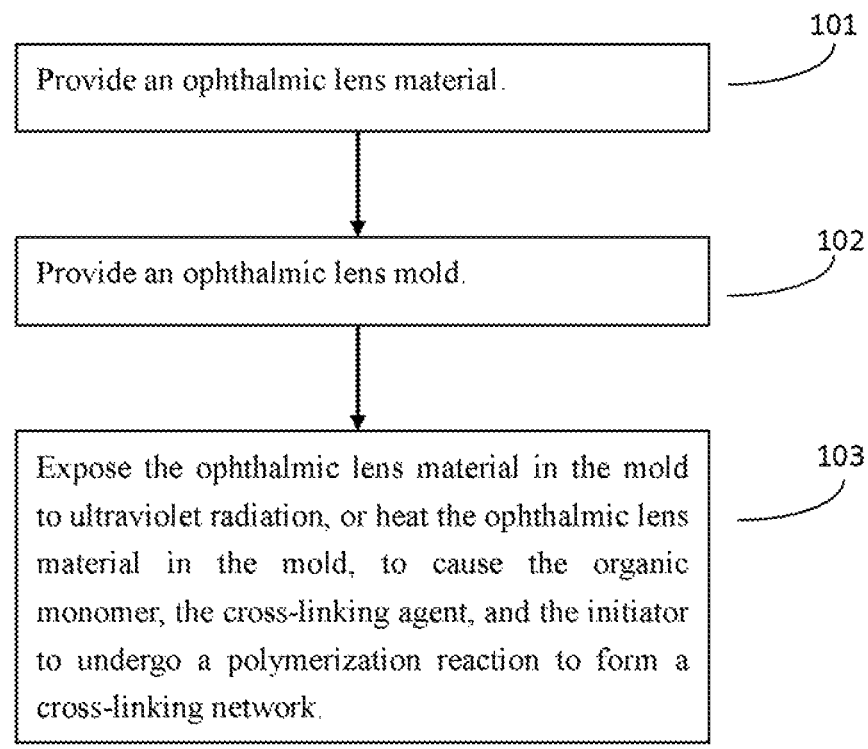

OPHTHALMIC LENS MATERIAL AND OPHTHALMIC LENS OF SUCH MATERIAL

This application claims benefit of Taiwanese Application No. 106102051 filed on Jan. 20, 2017, the entire contents of which is incorporated herein by references for all purposes.

FIELD

The subject matter generally relates to an ophthalmic lens material and an ophthalmic lens.

BACKGROUND

Ophthalmic lenses are worn by users to correct vision, or for cosmetic or therapeutic reasons. Since the ophthalmic lens directly contacts eyes of the user when in use, ophthalmic lens that can retain moisture for as long as possible is needed.

BRIEF DESCRIPTION OF THE DRAWING

Implementations of the present technology will now be described, by way of example only, with reference to the attached FIGURE.

FIG. 1 is a flow chart of an exemplary embodiment of a method for manufacturing an ophthalmic lens.

DETAILED DESCRIPTION

It will be appreciated that for simplicity and clarity of illustration, where appropriate, reference numerals have been repeated among the different FIGURES to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, methods, procedures, and components have not been described in detail so as not to obscure the related relevant feature being described. Also, the description is not to be considered as limiting the scope of the embodiments described herein. The drawings are not necessarily to scale, and the proportions of certain parts may be exaggerated to illustrate details and features of the present disclosure better.

Several definitions that apply throughout this disclosure will now be presented.

The term "comprising" when utilized, means "including, but not necessarily limited to"; it specifically indicates open-ended inclusion or membership in the so-described combination, group, series, and the like. The term "about" when utilized, means "not only include the numerical value, but also include numbers close to the numerical value".

An exemplary embodiment of an ophthalmic lens material comprises an organic monomer, a cross-linking agent, an initiator, a salt, and a solvent.

The organic monomer has a mass percentage of about 32% to about 81% of the total mass of the ophthalmic lens material. The cross-linking agent has a mass percentage of about 0.08% to about 14.6% of the total mass of the ophthalmic lens material. The initiator has a mass percentage of about 0.05% to about 12.1% of the total mass of the ophthalmic lens material. The salt has a mass percentage of about 3% to about 21.5% of the total mass of the ophthalmic lens material. The solvent has a mass percentage of about 5.5% to about 51% of the total mass of the ophthalmic lens material.

The organic monomer may be selected from 2-hydroxyethylmethacrylate (HEMA), methyl methacrylate (MMA), N,N-dimethyacrylamide (DMA), glycidyl methacrylate (GMA), N-vinyl-2-pyrrolidone (NVP), or any combination thereof.

The organic monomer further comprises an organic silicon monomer. The organic silicon monomer may be 3-(methacryloyloxy)propyltris(trimethylsiloxy)silane (TRIS).

The cross-linking agent may be selected from ethylene glycol dimethacrylate (EGDMA), trimethylolpropane trimethacrylate (TMPTMA), tri(ethylene glycol) dimethacrylate (TEGDMA), tri(ethylene glycol) divinyl ether (TEGDVE), trimethylene glycol dimethacrylate (TMGDMA), or any combination thereof.

The initiator may be a photo-initiator or a thermal initiator. The photo-initiator may be selected from benzoin methyl ether, diethoxyacetophenone, a benzoylphosphine oxide initiator, 1-hydroxycyclohexyl phenyl ketone, Darocure type initiator, Irgacure type initiator, or any combination thereof. In at least one exemplary embodiment, the photo-initiator is selected from Darocure-1173, Darocure-2959, Irgacure-1173, or any combination thereof. The benzoylphosphine oxide initiator may be selected from 2,4,6-trimethylbenzoyldiphenylophosphine oxide, bis-(2,6-dichlorobenzoyl)-4-N-propylphenylphosphine oxide, bis-(2,6-dichlorobenzoyl)-4-N-butylphenylphosphine oxide, or any combination thereof. The thermal initiator may be selected from 2,2'-azobis (2,4-dimethylpentanenitrile), 2,2'-azobis (2-methylpropanenitrile), 2,2'-azobis (2-methylbutanenitrile), azobisisobutyronite (AIBN), peroxides, or any combination thereof. In at least one exemplary embodiment, the peroxides may be benzoyl peroxide.

The salt may be selected from sodium chloride (NaCl), lithium chloride (LiCl), potassium acetate (KAc), magnesium chloride ($MgCl_2$), or any combination thereof.

The solvent may be water or a mixed solution comprising water and an alcohol. When the solvent is the mixed solution, a volume ratio of the water to the alcohol is about 1:100 to about 95:100.

The alcohol may be selected from ethanol, poly(ethylene glycol), poly(propylene glycol), 2-butanol, 2-propanol, p-menthan-3-ol, cyclohexyl alcohol, cyclopentanol, 2-pentanol, 3-pentanol, 2-hexanol, 3-hexanol, 3-methyl-2-butanol, 2-heptanol, 2-octanol, 2-nonanol, 2-decanol, 3-octanol, norborneol, tert-butanol, tert-amyl alcohol, 2-methyl-2-pentanol, 2,3-dimethyl-2-butanol, 3-methyl-3-pentanol, 1-methylcyclohexanol, 2-methyl-2-hexanol, 3,7-dimethyl-3-octanol, 1-chloro-2-methyl-2-propanol, 2-methyl-2-heptanol, 2-methyl-2-octanol, 2-2-methyl-2-nonanol, 2-methyl-2-decanol, 3-methyl-3-hexanol, 3-methyl-3-heptanol, 4-methyl-4-heptanol, 3-methyl-3-octanol, 4-methyl-4-octanol, 3-methyl-3-nonanol, 4-methyl-4-nonanol, 3-ethyl-3-hexanol, 3-methyl-3-heptanol, 4-ethyl-4-heptanol, 4-propyl-4-heptanol, 4-isopropyl-4-heptanol, 2,4-dimethyl-2-pentanol, 1-methylcyclopentanol, 1-ethylcyclopentanol, 4-hydroxy-4-methyl-1-cyclopentanol, 2-phenyl-2-propanol, 2-methoxy-2-methyl-2-propanol 2,3,4-trimethyl-3-pentanol, 3,7-dimethyl-3-octanol, 2-phenyl-2-butanol, 2-methyl-1-phenyl-2-propanol and 3-ethyl-3-pentanol, 1-ethoxy-2-propanol, 1-methyl-2-propanol, isopropanol, or any combination thereof.

In the ophthalmic lens material, the salt can be dissolved in the water, and a plurality of anions and cations are dissociated. The water comprises a plurality of water molecules. The anions and cations can be bonded to the water molecules, thereby the anions and cations can have a strong binding strength with the water molecules. The anions and cations can be bonded to the water molecules easily, an ionic hydration degree of the water molecules is high. Water evaporation is very slow because of the high strength of the bond between the water molecules and the anions and cations. The slow evaporation rate retains the moisture of the ophthalmic lens material for a long period of time.

An ophthalmic lens formed by the ophthalmic lens material is provided. The ophthalmic lens comprises a cross-linking network, a plurality of water molecules dispersed in the cross-linking network, and a plurality of anions and cations dispersed in the cross-linking network and bonded to the water molecules. The cross-linking network is formed by exposing the ophthalmic lens material to ultraviolet radiation or heating the ophthalmic lens material. The radiation or heating causes the organic monomer, the cross-linking agent, and the initiator to undergo a polymerization reaction. The plurality of anions and cations are dissociated from the salt. The water molecules comes from the water. Although the water molecules tend to evaporate, the water molecules need to overcome the binding strength with the anions and cations, and remove the anions and cations. Thereby, evaporation of the water is more difficult to achieve, and the evaporation rate of the water is reduced, thus, the ophthalmic lens can retain moisture for a long time.

FIG. 1 illustrates a flowchart of a method for manufacturing the ophthalmic lens in accordance with an exemplary embodiment. The exemplary method is provided by way of example, as there are a variety of ways to carry out the method. Each block shown in FIG. 1 represents one or more processes, methods or subroutines, carried out in the exemplary method. Furthermore, the illustrated order of blocks is by example only, and the order of the blocks can change. Additional blocks may be added, or fewer blocks may be utilized, without departing from this disclosure. The exemplary method may begin at block 101.

At block 101, an ophthalmic lens material is provided. The ophthalmic lens material comprises an organic monomer, a cross-linking agent, an initiator, a salt, and a solvent. The organic monomer has a mass percentage of about 32% to about 81% of the total mass of the ophthalmic lens material. The cross-linking agent has a mass percentage of about 0.08% to about 14.6% of the total mass of the ophthalmic lens material. The initiator has a mass percentage of about 0.05% to about 12.1% of the total mass of the ophthalmic lens material. The salt has a mass percentage of about 3% to about 21.5% of the total mass of the ophthalmic lens material. The solvent has a mass percentage of about 5.5% to about 51% of the total mass of the ophthalmic lens material.

At block 102, an ophthalmic lens mold is provided, and the ophthalmic lens material is placed into the mold.

At block 103, the ophthalmic lens material in the mold is exposed to ultraviolet radiation or is heated, to cause the organic monomer, the cross-linking agent, and the initiator to undergo a polymerization reaction to form a cross-linking network. A plurality of water molecules are dispersed in the cross-linking network, and a plurality of anions and cations dissociated by the salt are dispersed in the cross-linking network and bonded to the water molecules, thereby forming the ophthalmic lens.

Example 1

The ophthalmic lens material comprised HEMA, TMPTMA, Irgacure-1173, LiCl and water.

The HEMA had a mass percentage of 53.4% of the total mass of the ophthalmic lens material, the TMPTMA had a mass percentage of 0.53% of the total mass of the ophthalmic lens material, the Irgacure-1173 had a mass percentage of 0.23% of the total mass of the ophthalmic lens material, the LiCl had a mass percentage of 12.7% of the total mass of the ophthalmic lens material, and the water had a mass percentage of 33.14% of the total mass of the ophthalmic lens material.

Example 2

The ophthalmic lens material comprised HEMA, TMPTMA, Irgacure-1173, $MgCl_2$ and water.

The HEMA had a mass percentage of 58.34% of the total mass of the ophthalmic lens material, the TMPTMA had a mass percentage of 0.545% of the total mass of the ophthalmic lens material, the Irgacure-1173 had a mass percentage of 0.254% of the total mass of the ophthalmic lens material, the $MgCl_2$ had a mass percentage of 12.45% of the total mass of the ophthalmic lens material, and the water had a mass percentage of 28.411% of the total mass of the ophthalmic lens material.

Example 3

The ophthalmic lens material comprised HEMA, MAA, NVP, TMPTMA, AIBN, LiCl and a mixed solution of water and ethanol. The volume ratio of the water to the ethanol was 65:100.

The HEMA had a mass percentage of 52.43% of the total mass of the ophthalmic lens material, the MAA had a mass percentage of 0.82% of the total mass of the ophthalmic lens material, the NVP had a mass percentage of 1.05% of the total mass of the ophthalmic lens material, the TMPTMA had a mass percentage of 0.55% of the total mass of the ophthalmic lens material, the AIBN had a mass percentage of 0.26% of the total mass of the ophthalmic lens material, the LiCl had a mass percentage of 10.87% of the total mass of the ophthalmic lens material, and the mixed solution of water and ethanol had a mass percentage of 34.01% of the total mass of the ophthalmic lens material.

Example 4

The ophthalmic lens material comprised HEMA, MAA, NVP, TMPTMA, Irgacure-1173, KAc and a mixed solution of water and ethanol. The volume ratio of the water to the ethanol was 5:100.

The HEMA had a mass percentage of 45.77% of the total mass of the ophthalmic lens material, the MAA had a mass percentage of 0.71% of the total mass of the ophthalmic lens material, the NVP had a mass percentage of 0.93% of the total mass of the ophthalmic lens material, the TMPTMA had a mass percentage of 0.49% of the total mass of the ophthalmic lens material, the Irgacure-1173 had a mass percentage of 0.22% of the total mass of the ophthalmic lens material, the KAc had a mass percentage of 22.15% of the total mass of the ophthalmic lens material, and the mixed solution of water and ethanol had a mass percentage of 29.73% of the total mass of the ophthalmic lens material.

Example 5

The ophthalmic lens material comprised HEMA, TRIS, DMA, TMPTMA, Irgacure-1173, LiCl and a mixed solution of water and 2-hexanol. The volume ratio of the water to the 2-hexanol was 95:100.

The HEMA had a mass percentage of 12.1% of the total mass of the ophthalmic lens material, the TRIS had a mass percentage of 41.9% of the total mass of the ophthalmic lens material, the DMA had a mass percentage of 0.8% of the total mass of the ophthalmic lens material, the TMPTMA had a mass percentage of 0.38% of the total mass of the ophthalmic lens material, the Irgacure-1173 had a mass percentage of 0.31% of the total mass of the ophthalmic lens material, the LiCl had a mass percentage of 11.9% of the total mass of the ophthalmic lens material, and the mixed solution of water and 2-hexanol had a mass percentage of 32.61% of the total mass of the ophthalmic lens material.

The embodiments shown and described above are only examples. Even though numerous characteristics and advantages of the present technology have been set forth in the foregoing description, together with details of the structures and function of the present disclosure, the disclosure is illustrative only, and changes can be made in the detail, including in matters of shape, size, and arrangement of the parts within the principles of the present disclosure, up to and including the full extent established by the broad general meaning of the terms used in the claims.

What is claimed is:

1. An ophthalmic lens material comprising:
   an organic monomer having a mass percentage of about 32% to about 81% of the total mass of the ophthalmic lens material;
   a cross-linking agent having a mass percentage of about 0.08% to about 14.6% of the total mass of the ophthalmic lens material;
   an initiator having a mass percentage of about 0.05% to about 12.1% of the total mass of the ophthalmic lens material;
   a salt having a mass percentage of about 3% to about 21.5% of the total mass of the ophthalmic lens material, the salt selected from a group consisting of sodium chloride, lithium chloride, potassium acetate, magnesium chloride, and any combination thereof; and
   a solvent having a mass percentage of about 5.5% to about 51% of the total mass of the ophthalmic lens material, the solvent comprising water.

2. The ophthalmic lens material of claim 1, wherein the organic monomer is selected from a group consisting of 2-hydroxyethylmethacrylate, methyl methacrylate, N,N-dimethyacrylamide, glycidyl methacrylate, N-vinyl-2-pyrrolidone, and any combination thereof.

3. The ophthalmic lens material of claim 2, wherein the organic monomer further comprises an organic silicon monomer, the organic silicon monomer is 3-(methacryloyloxy)propyltris(trimethylsiloxy)silane.

4. The ophthalmic lens material of claim 1, wherein the cross-linking agent is selected from a group consisting of ethylene glycol dimethacrylate, trimethylolpropane trimethacrylate, tri(ethylene glycol) dimethacrylate, tri(ethylene glycol) divinyl ether, trimethylene glycol dimethacrylate, and any combination thereof.

5. The ophthalmic lens material of claim 1, wherein the initiator is photo-initiator, the photo-initiator is selected from a group consisting of benzoin methyl ether, diethoxyacetophenone, a benzoylphosphine oxide initiator, 1-hydroxycyclohexyl phenyl ketone, and any combination thereof, the benzoylphosphine oxide initiator is selected from a group consisting of 2,4,6-trimethylbenzoyldiphenylophosphine oxide, bis-(2,6-dichlorobenzoyl)-4-N-propylphenylphosphine oxide, bis-(2,6-dichlorobenzoyl)-4-N-butylphenylphosphine oxide, and any combination thereof.

6. The ophthalmic lens material of claim 1, wherein the initiator is thermal initiator, the thermal initiator is selected from a group consisting of 2,2'-azobis (2,4-dimethylpentanenitrile), 2,2'-azobis (2-methylpropanenitrile), 2,2'-azobis (2-methylbutanenitrile), azobisisobutyronite, peroxides, and any combination thereof.

7. The ophthalmic lens material of claim 1, wherein the salt is lithium chloride.

8. The ophthalmic lens material of claim 1, wherein the solvent further comprises an alcohol.

* * * * *